United States Patent [19]

Schweigl et al.

[11] Patent Number: 4,899,914
[45] Date of Patent: Feb. 13, 1990

[54] METHOD FOR PRODUCING A STERILE PRESERVATIVE-FREE AEROSOL SALINE SOLUTION

[75] Inventors: Erwin Schweigl, Bramalea; Thomas P. Hayes, Waterdown; Dusan Kljajic, Etobicoke; Rolf Jellositz, Mississauga, all of Canada

[73] Assignee: CIBA-Geigy Corporation, Ardsley, N.Y.

[21] Appl. No.: 267,025

[22] Filed: Nov. 4, 1988

[51] Int. Cl.$^4$ .................... B65B 31/02; B65D 83/14
[52] U.S. Cl. ........................ 222/394; 53/428; 53/470; 206/524.1; 222/1
[58] Field of Search ............. 222/1, 394; 53/111 RC, 53/428, 431, 432, 470, 474; 141/3; 206/524.1

[56] References Cited

U.S. PATENT DOCUMENTS

| | | | |
|---|---|---|---|
| 3,069,319 | 12/1962 | Stearns | 53/470 X |
| 3,117,404 | 1/1964 | Miles | 53/470 |
| 3,189,231 | 6/1965 | Kibbel et al. | 53/470 X |
| 3,216,463 | 11/1965 | Kibbel et al. | 141/3 |
| 3,763,900 | 10/1973 | Solms-Baruth et al. | 141/3 |
| 3,896,602 | 7/1975 | Petterson | 53/411 |
| 4,521,375 | 6/1985 | Houlsby | 422/29 |
| 4,585,488 | 4/1986 | Giefer | 134/27 |

*Primary Examiner*—Robert L. Spruill
*Assistant Examiner*—Linda B. Johnson
*Attorney, Agent, or Firm*—Irving M. Fishman

[57] ABSTRACT

Described is a method, and resulting product, for producing a sterile preservative-free areosol contact lens solution comprising; aseptically filling a pre-sterilized aerosol container with a contact lens solution preserved with sufficient hydrogen peroxide; aseptically introducing into the container means, such as a catalyst, for converting the hydrogen peroxide into inert or inactive substances one of which is a suitable propellant; and sealing and storing the container for a time sufficient to complete the inactivation of the hydrogen peroxide and creation of the suitable propellant.

10 Claims, No Drawings

METHOD FOR PRODUCING A STERILE PRESERVATIVE-FREE AEROSOL SALINE SOLUTION

FIELD OF THE INVENTION

This invention relates to a method for producing a sterile, preservative-free, aerosol saline solution product for use by contact lens wearers, and more particularly to a method which utilizes a preservative together with means for converting the preservative into an inert substance which becomes the propellant of the aerosol product.

BACKGROUND OF THE INVENTION

Wearers of contact lenses, must regularly rinse their lenses with a saline solution prior to inserting the lenses for continued use. For example, contact lenses must be rinsed after subjecting the lenses to a variety of chemical disinfection regimens necessary to rid the lenses of pathogenic micro-organisms. The saline solution typically has the same isotonicity as human tears to minimize occular irritation in the user. Rinsing the lenses with a normal saline solution will wash away potentially harmful and irritating chemicals remaining on the lenses as a result of a disinfection regimen.

Contact lens users generally react unfavourably, by experiencing untoward reactions, to the presence of a variety of preservatives commonly used in contact lens solutions, including normal saline solutions. It is desirable therefore to be able to produce contact lens products, including normal saline solutions, which are sterile, yet free of preservatives. Such solutions must be sterile in order not to introduce harmful micro-organisms into the eyes of the contact lens user.

It is known in the prior art (see Giefer, U.S. Pat. No. 4,585,488 issued 29 Apr. 1986) to place a saline solution preserved with hydrogen peroxide into a container together with a disk coated with platinum. The platinum reacts (as a catalyst) with the hydrogen peroxide to cause this preservative to become inert by splitting it into water ($H_2O$) and oxygen ($O_2$) gas. The complete reaction is as follows:

$$2H_2O_2 + \text{Platinum Catalyst} \rightarrow 2H_2O_2 + O_2$$

The prior art method utilizing the above reaction involves the contact lens user adding the solution preserved with hydrogen peroxide to a non-sterile container, placing the platinum coated disk into the container, adding the contact lenses to the container and leaving the lenses to soak over night, so that by the next morning, the hydrogen peroxide will have been converted into inert water and the lenses will be soaking in pure saline solution. The contact lens user would then merely insert the lenses without risk of irritation from chemical preservatives. This prior art method is however, cumbersome, awkward and time consuming.

It is also known in the prior art to modify the aforesaid method by utilizing sodium pyruvate to decompose the hydrogen peroxide (see Houlsby, U.S. Pat. No. 4,521,375 issued 4 June, 1985). The sodium pyruvate reacts with the hydrogen peroxide to produce inert by-products including water and carbon dioxide.

It is further known in the prior art to fill an aerosol can with normal saline solution and a propellant, and then to subject the sealed aerosol can to terminal sterilization by irradiating it with gamma rays. This results in a sterile aerosol product containing normal saline solution, and free of any chemical preservatives. Such prior art aerosol products require the addition of a propellant, such as nitrogen, in order to achieve the pressure levels necessary for proper aerosol functioning. The disadvantages of such prior art irradiated aerosol products are several. Firstly, it is very expensive to conduct terminal sterilization by irradiation using gamma rays. Secondly, there are safety and hence political concerns relating to the use of radiation to sterilize products for use in the human body. Lastly, there are several practical problems related to the use of radiation, including the need to irradiate the aerosol product very shortly after the aerosol container has been filled and the fact that use of radiation on some chemicals will cause the chemicals to breakdown. This limits which chemicals may be used in such products to be sterilized by radiation.

An additional problem present in the prior art aerosol products relates to the difficulty in obtaining U.S. Federal Drug Administration approval for aseptic packaging of unpreserved solutions for ophthalmic use.

It is desirable to have sterile, preservative-free ophthalmic product in aerosol dispensing containers in order to maintain product sterility during use. Because the aerosol container is under pressure, there is minimal risk of micro-organisms being able to enter the sterile environment inside the aerosol can during its use. Ophthalmic solutions housed in plastic squeeze bottles may easily become contaminated during use, due to reflux action of the liquid during dispensing of the solution by the contact lens user. As a result of the aforesaid disadvantages, there is a need for an economical, safe and effective ophthalmic saline solution in aerosol packaging, which is free of chemical preservatives at the time of use of the solution by the contact lens wearer, without having been subjected to radiation exposure.

SUMMARY OF THE DISCLOSURE

In its broadest aspect, this invention teaches combining a preservative in an aerosol container with means for converting the preservative into an inert or inactive substance, which substance is suitable to act as the propellant of the aerosol product.

More particularly, this invention provides a method for producing a sterile preservative-free aerosol saline solution comprising; aseptically filling a pre-sterilized aerosol container with a saline solution preserved with sufficient hydrogen peroxide; aseptically introducing into the aerosol container means for converting the hydrogen peroxide into inert or inactive substances one of which is a suitable propellant; and sealing and storing the container for a time sufficient to complete the inactivation of the hydrogen peroxide and creation of the suitable propellant.

The invention is particularly applicable to making products for use by contact lens users including saline solutions. The invention is further applicable to the preparation of aseptic medicinal burn (or other medicinal) sprays and aerosol food products (where the food product is compatible with hydrogen peroxide). Still further the invention is applicable to the preparation of preservative-free cosmetic products in aerosol or atomizer type containers.

The means utilized for converting the hydrogen peroxide into inert by-products may be several. Preferred is the use of platinum which acts as a catalyst to convert the hydrogen peroxide into aqueous water and oxygen gas. Sufficient hydrogen peroxide must be used in order to provide acceptable preservation of the solution and furthermore to produce sufficient oxygen gas by-product to act as the propellant of the solution in the aerosol product. Also preferred is the use of catalase enzyme as the means for converting the hydrogen peroxide to inert substances.

Other means for converting the hydrogen peroxide to inert substances include the use of sodium pyruvate. When sodium pyruvate is used, the resulting propellant is carbon dioxide gas.

The invention also contemplates aerosol type products produced by the various method disclosed herein.

DETAILED DESCRIPTION OF THE INVENTION

In the most preferred embodiment the invention utilizes the following chemical reaction: :

$$2H_2O_2 + \text{Platinum Catalyst} \rightarrow 2H_2O + O_2$$

The hydrogen peroxide is aseptically added to the normal saline or other type of solution in a pre-sterilized aerosol type container which is often a can. The platinum catalyst may be utilized in a variety of forms including a disk coated with platinum and commercially available and known as they AO Disc (registered trade mark of CIBA Vision Corporation). Sufficient hydrogen peroxide must be added to obtain the desired preservation characteristics. Furthermore, sufficient hydrogen peroxide must be present to provide enough oxygen (or other suitable) gas to act as propellant of the ultimate aerosol product. Sufficient propellant must be present to expel, under pressure substantially the entire contents of the aerosol or other type of spray product. The platinum catalyst when employed as a platinum coated disc may be inserted into the aerosol container where it is free to move about the contents thereof when the container is agitated. As a catalyst, the platinum is utilized in the chemical reaction without contaminating the solution being the end product of the reaction resulting from the inactivation of the hydrogen peroxide.

Once all ingredient components have been added to the container, it is aseptically sealed and stored for a time sufficient to allow for both the inactivation of the hydrogen peroxide to be completed and the creation of sufficient propellant, all prior to use of the product by the contact lens wearer (as the case may be).

By way of examples set out hereinafter, there are variations of the method of the invention as well as calculations employed in determining quantities of preservative to be used.

EXAMPLE 1

When using catalase enzyme to inactivate the hydrogen peroxide, the following chemical reaction takes place:

$$2H_2O_2 + \text{Catalase Enzyme} \rightarrow 2H_2O + O_2$$

The catalase enzyme promotes the decomposition of the hydrogen peroxide to water and oxygen gas. Catalase enzymes are available from a variety of sources such as animals, plants, bacteria and fungi. Because catalase reacts immediately with hydrogen peroxide, when using catalase the following procedure is recommended. The can should be capped after being filled with hydrogen peroxide and normal saline (or other substance). Thereafter the catalase may be injected through the valve into the can preferrably using aseptic technique in a clean room.

EXAMPLE 2

When sodium pyruvate is employed in the performance of the method of the invention, the following chemical reaction occurs:

$$H_2O_2 + CH_3COCO_2Na \rightarrow CH_3CO_2Na + CO_2 + H_2O$$

It will be apparent from the above chemical reaction, that the use of sodium pyruvate to inactivate the hydrogen peroxide results in the propellant being carbon dioxide gas instead of oxygen.

EXAMPLE 3

The following calculations illustrate the quantity of hydrogen peroxide required to pressurize an aerosol can containing saline solution.

assume that the can has an internal volume of 560 ml.

if the can is filled with 360 ml of solution, the resulting headspace will be 200 ml.

assume that the oxygen produced by the decomposition of peroxide behaves like an ideal gas.

therefore by the ideal gas law.

$$PV = nRT$$

where P = pressure (atmospheres)
V = volume ($cm^3$)
n = amount of gas (gram moles)
T = temperature (Kelvins)
R = gas constant - 82.05

$$\frac{cm^3 \cdot atm}{g \cdot mole \cdot K}$$

assuming the following conditions:
V = 200 ml
P = 90 psig (6.12 atm)
T = 20° C. (293° K.)

by the ideal gas law, n = 0.0509 g.moles of oxygen.

based on the stochiometry of the reaction, the required amount of hydrogen peroxide is 0.102 g.moles; this converts to 3.46 g of hydrogen peroxide.

typically, the hydrogen peroxide is in a 35% w/v solution.

therefore the required volume of solution is 9.9 ml.

This calculation has shown that in order to pressurize a can to an internal pressure of 90 psig at 20° C., 9.9 ml of 35% (w/v) peroxide solution should be added to the saline solution.

Experiments have shown that these calculations are an accurate representation of the actual reaction.

Presently the only unpreserved contact lens solutions marketed are either blow fill sealed or are subjected to terminal sterilization by irradiation. The blow fill sealed technique is currently used for aseptically packaged unpreserved solutions since the process involves no human intervention. When using terminal sterilization, the product is not aseptically filled but rather the packaged product is subjected to sterilization by irradiation with gamma rays which will destroy all microbiological activity.

In a conventional bottle filling operation, human intervention in a clean room prevents FDA approval of packaging aseptically unpreserved solutions.

The method of the instant invention has overcome the prior art problems by utilizing the method of the invention as hereinbefore described.

The instant invention contemplates not only the method described herein, but in addition contemplates the end product, namely a preservative free aerosol product when prepared by the method described.

It will be apparent to those skilled in the art that other catalysts or reducing agents, beyond those mentioned herein, may be utilized in the working of this invention.

Furthermore, it should be noted that this invention has application beyond the preparation of contact lens solutions. For example, burn products are preferred in aerosol form, in order to provide uniform and painless application to the burn area. Using the methods of the instant invention, it is possible to provide a sterile, preservative-free aerosol burn spray as follows:

$$Medicament + 2H_2O_2 + Platinum\ Catalyst \rightarrow 2H_2O + O_2 + Medicament$$

The method of the instant invention has further application to food products. Utilizing the invention it is possible to incorporate food products compatible with hydrogen peroxide into an aerosol or other spray type container. After the hydrogen peroxide has been inactivated by a catalyst or reducing agent, the food product may be sprayed from the container and incorporated into other foods or directly consumed by humans, for example, in accordance with the following chemical reaction:

$$2H_2O_2 + catalyst\ or\ reducing\ agent + compatible\ food \rightarrow 2H_2O + O_2 + food$$

Many users of cosmetic products suffer allergic (dermatological reactions) to ingredients of such products including preservatives. Using the methods of the instant invention, it is possible to provide a sterile, preservative-free cosmetic spray product. An example of such a reaction follows:

$$2H_2O_2 + catalyst + compatible\ cosmetic \rightarrow 2H_2O + O_2 + cosmetic$$

It should further be obvious to those skilled in the art that such aerosol products need not be restricted to substances conventionally regarded as "solutions", but rather may include, foams, a variety of emulsions or any other liquid or semi-liquid composition compatible with an aerosol or other spray type of product.

It will also be obvious to those skilled in the art that the invention herein may also work with preservatives other than hydrogen peroxide, as long as such preservatives are capable of reaction to inert substances one of which is a propellant.

We claim:

1. A method for producing a sterile preservative-free aerosol product comprising:
   (a) aseptically filling a presterilized aerosol container with a solution preserved with sufficient hydrogen peroxide, said solution containing or mixed with the product to be dispensed;
   (b) aseptically introducing into the aerosol container means for converting the hydrogen peroxide into inert substances one of which is a propellant; and
   (c) sealing and storing the aerosol container for a time sufficient to allow complete inactivation of the hydrogen perixode and creation of sufficient propellant to dispense the product from said aerosol container.

2. The method of claim 1 wherein the means for converting the hydrogen peroxide into inert substances is a catalyst or a reducing agent.

3. The method of claim 2 wherein the catalyst or reducing agent is platinum.

4. The method of claim 2 wherein the catalyst or reducing agent is sodium pyruvate.

5. The method of claim 2 wherein the aerosol product contains normal saline, and the catalyst or reducing agent is platinum.

6. The method of claim 2 wherein the catalyst or reducing agent is catalase, and the container is sealed prior to the introduction of the catalase into the container.

7. The method of claims 3, 4 or 6 wherein the product to be dispensed comprises a medicinal spray, a food or a cosmetic.

8. The method of claim 6 wherein the container is an aerosol can with a valve and the catalase is introduced into the sealed can by injecting it into the can through the valve.

9. A sterile preservative-free aerosol product produced by the method of any one of claims 1 to 6 and 8.

10. A sterile preservative-free aerosol product produced by the method of claim 7.

* * * * *